United States Patent
Freeman et al.

(10) Patent No.: US 11,980,482 B2
(45) Date of Patent: *May 14, 2024

(54) CIRCUITS AND METHODS FOR ELECTROSURGICAL UNIT SIGNAL DETECTION

(71) Applicant: DRÄGERWERK AG & CO. KGAA, Lübeck (DE)

(72) Inventors: Daniel K. Freeman, Reading, MA (US); Ronald Gatzke, Lexington, MA (US)

(73) Assignee: DRÄGERWERK AG & CO. KGAA, Lübeck (DE)

(*) Notice: Subject to any disclaimer, the term of this patent is extended or adjusted under 35 U.S.C. 154(b) by 351 days.

This patent is subject to a terminal disclaimer.

(21) Appl. No.: 17/400,960

(22) Filed: Aug. 12, 2021

(65) Prior Publication Data

US 2021/0369206 A1 Dec. 2, 2021

Related U.S. Application Data

(63) Continuation of application No. 16/063,178, filed as application No. PCT/US2015/066382 on Dec. 17, 2015, now Pat. No. 11,103,190.

(51) Int. Cl.
*A61B 5/00* (2006.01)
*A61B 5/30* (2021.01)
*A61B 5/301* (2021.01)
*A61B 5/369* (2021.01)
*A61B 18/16* (2006.01)
*A61B 18/00* (2006.01)

(52) U.S. Cl.
CPC .............. *A61B 5/7217* (2013.01); *A61B 5/30* (2021.01); *A61B 5/301* (2021.01); *A61B 5/369* (2021.01); *A61B 5/7225* (2013.01); *A61B 5/725* (2013.01); *A61B 18/16* (2013.01); *A61B 2018/00839* (2013.01); *A61B 2505/05* (2013.01)

(58) Field of Classification Search
CPC .................................... A61B 5/7217
USPC ........................................ 600/509
See application file for complete search history.

(56) References Cited

U.S. PATENT DOCUMENTS

2009/0018429 A1* 1/2009 Saliga .................... A61B 5/725
600/407

* cited by examiner

*Primary Examiner* — Nicole F Lavert
(74) *Attorney, Agent, or Firm* — Nolte Lackenbach Siegel

(57) ABSTRACT

Circuits are provided for detecting an electrosurgical unit signal. An example circuit includes: a filter configured to process a floating ground signal associated with measuring a bio-potential signal of a patient, and a detector configured to output a sensing signal based at least in part on the floating grounding and the Earth ground for detecting an electrosurgical unit signal.

17 Claims, 4 Drawing Sheets

$V_1$ = DIFFERENTIAL SENSE $V_2$ = COMMON MODE SENSE

CIRCUITS AND METHODS FOR ELECTROSURGICAL UNIT SIGNAL DETECTION

CROSS REFERENCE TO RELATED APPLICATION

This application is a continuation of co-pending U.S. patent application Ser. No. 16/063,178, filed Jun. 15, 2018, the entire contents of which is hereby incorporated by reference as though fully set forth herein. Application Ser. No. 16/063,178 is a national stage application, filed under U.S.C. 371, of International Application No. PCT/US2015/0066382, filed Dec. 17, 2015, the entire contents of which is hereby incorporated by reference herein.

TECHNICAL FIELD

The subject matter described herein relates generally to electric circuits, and, more specifically, to signal detection circuits.

BACKGROUND

Electrosurgical units ("ESU") are routinely used in operating rooms and are known to interfere with the monitoring of patients' bio-potential signals (e.g. electrocardiogram signals, electroencephalography signals, blood pressure, etc.). An ESU applies a large amplitude (e.g., 100 V-5 kV) and high frequency (>300 kHz) signal to a patient's body for operations. However, the ESU signal may also have energy at lower frequencies (e.g., from direct current to 100 Hz) because the high-frequency ESU signal amplitude is modulated due to cutting and subsequently rectified when a current passes through ESU electrodes. As a result, the lower frequency components of the ESU signal may generate noises in the pass band of bio-potential signals of interest. Such noise often produces false alarms (e.g., a high heart rate) in software algorithms that monitor the bio-potential signals.

SUMMARY

Circuits and methods are provided for detecting an electrosurgical unit signal. An example circuit for detecting an electrosurgical unit signal includes: a filter configured to process a floating ground signal associated with measuring a bio-potential signal of a patient; and a detector configured to output a sensing signal based at least in part on the floating ground signal and an Earth ground for detecting an electrosurgical unit signal.

As an example, the filter includes: a capacitor; and a resistor including a first resistor terminal and a second resistor terminal, the first resistor terminal being electrically connected to the capacitor, the second resistor terminal being biased to the Earth ground. As another example, the capacitor includes a first capacitor terminal and a second capacitor terminal; the first capacitor terminal is configured to receive the floating ground signal; and the second capacitor terminal is electrically connected to the first resistor terminal.

For example, the detector includes: a diode including an anode terminal and a cathode terminal, the anode terminal being electrically connected to the filter; a capacitor including a first capacitor terminal and a second capacitor terminal, the first capacitor terminal being electrically connected to the cathode terminal, the second capacitor terminal being biased to the Earth ground; and a resistor including a first resistor terminal and a second resistor terminal, the first resistor terminal being electrically connected to the first capacitor terminal, the second resistor terminal being biased to the Earth ground.

In another example, the floating ground signal includes a high-frequency component and a low-frequency component; and the filter is configured to pass the high-frequency component and block the low-frequency component. In yet another example, the low-frequency component is associated with the bio-potential signal of the patient.

For example, the high-frequency component corresponds to a frequency value larger than a threshold; and the low-frequency component corresponds to a low frequency value smaller than the threshold. As another example, the detector is further configured to rectify the filtered floating ground signal to a direct current level.

In a specific example, the electrosurgical unit signal is detected when the direct current level is higher than a threshold. For example, a neutral drive amplifier is configured to receive the floating ground signal as an input. In one example, the detector includes a half-wave rectifier. In another example, the detector includes a full-wave rectifier. In yet another example, the detector includes a self-clocked demodulator.

In a particular example, the circuit further includes: a signal processor configured to process the bio-potential signal according to an algorithm. As an example, the signal processor is further configured to change the algorithm based at least in part on the electrosurgical unit signal. In another example, the signal processor is further configured to change the algorithm linearly or non-linearly. For example, the bio-potential signal corresponds to an electrocardiogram signal. In another example, the bio-potential signal corresponds to an electroencephalography signal. In a specific example, the filter and the detector are placed in an electrical isolation region where a monitor for the bio-potential signal is located.

An example method is provided for detecting an electrosurgical unit signal. The method includes: processing a floating ground signal associated with measuring a bio-potential signal of a patient; and outputting a sensing signal based at least in part on the floating grounding and the Earth ground for detecting an electrosurgical unit signal. For example, the method is implemented using the example circuit as described above.

The subject matter described herein provides many technical advantages. For example, the circuits described herein are inexpensive in that high-cost ADCs (analog to digital converters) for sampling MHz signals are not used. Also, the circuits described herein can be more reliable than software algorithms which often depend on complex nonlinear filtering at electrodes. Furthermore, voltages can be measured relative to a floating ground (not the Earth ground), and the circuitry described herein can be placed within the same electrical isolation region of a bio-potential monitoring circuitry, so as to greatly simplify circuit design.

The details of one or more variations of the subject matter described herein are set forth in the accompanying drawings and the description below. Other features and advantages of the subject matter described herein will be apparent from the description and drawings, and from the claims.

DETAILED DESCRIPTION

The interference of an ESU with bio-potential signal monitoring can be problematic. For example, false alarms may be produced when an ESU is in use, but alarm mechanisms may not be turned off to prevent such false alarms because the alarm mechanisms are still needed in between the use of the ESU. Software algorithms may be developed to detect an ESU in operation, but such algorithms may be inherently limited by the sampling rate of an ADC used for converting ESU signals to digital signals. Usually, the sampling rate of the ADC is too low to detect high-frequency ESU signals which are often in the MHz range.

The systems and methods described herein can be configured to implement various mechanisms for detecting whether an ESU is active. For example, the unique high frequency nature of ESU signals, usually separated from bio-potential signal related frequencies by more than two orders of magnitude, renders the high frequency ESU signals available for detection.

Figure 1:
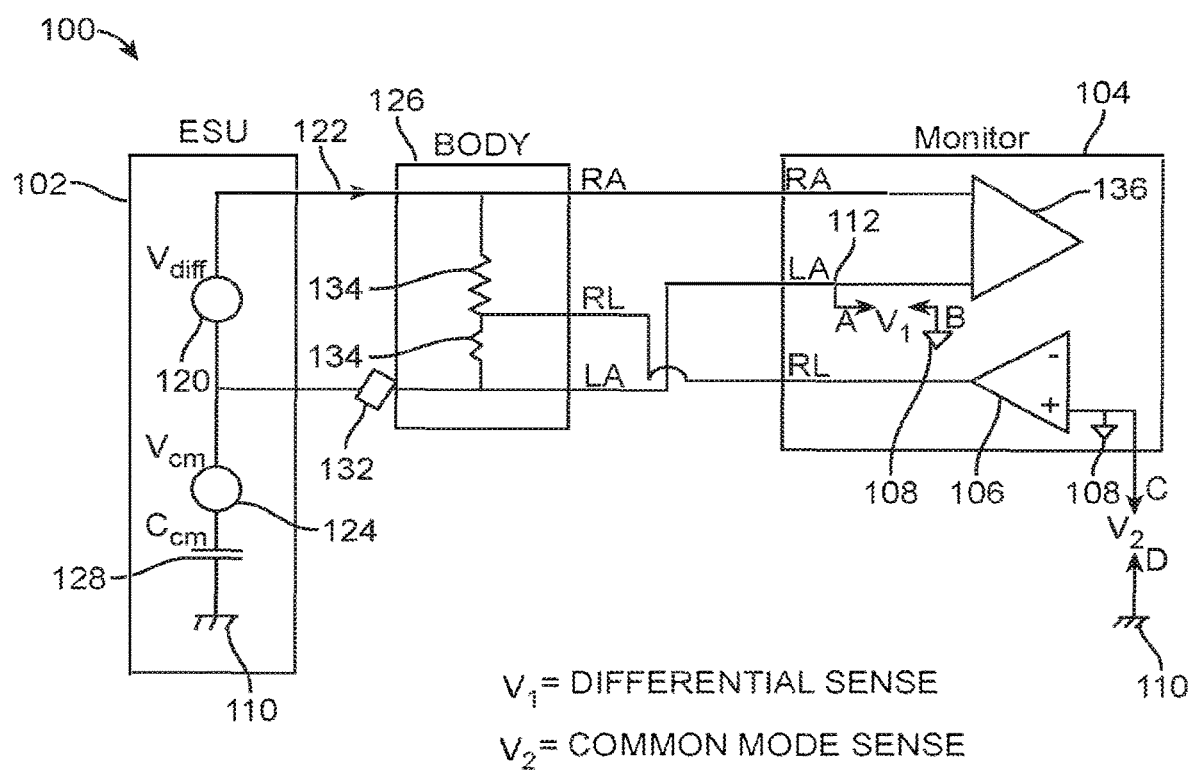
FIG. 1 depicts an example diagram for ESU signal detection.
Figure 2:
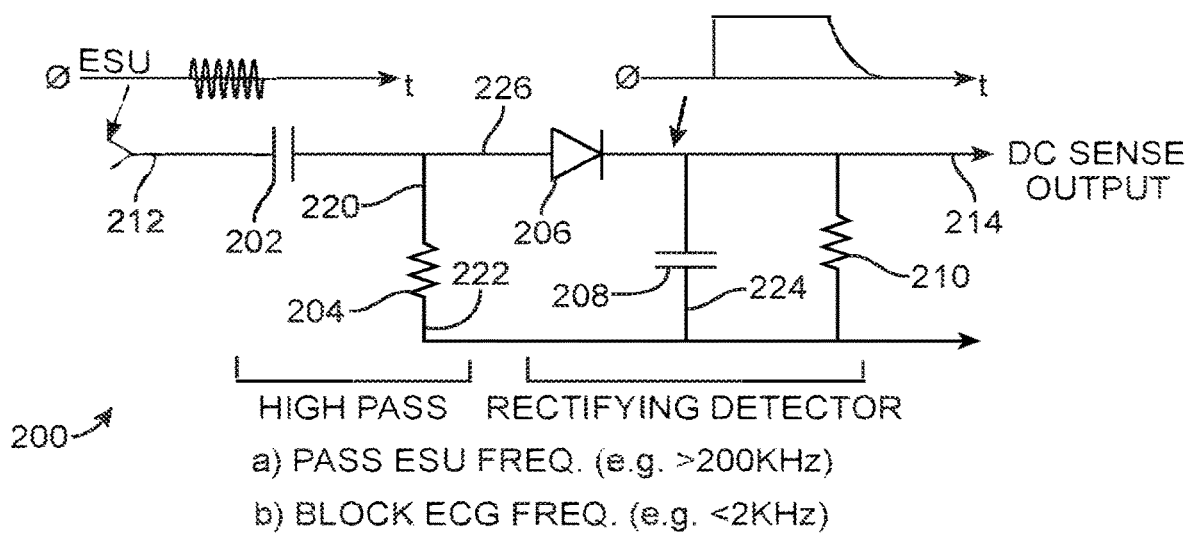
FIG. 2 depicts an example diagram showing an ESU detection circuit.

FIG. 1 depicts an example diagram for ESU signal detection. As shown in FIG. 1, a circuit 100 includes an ESU 102 and a bio-potential monitoring system 104. The circuit 100 can implement two ESU signal detection mechanisms: differential sensing and common mode sensing. For differential sensing, a sensing circuit (e.g., as shown in FIG. 2) can be connected between a bio-potential input terminal (e.g., point "A") and a floating ground 108 (e.g., point "B"), where the floating ground 108 corresponds to a floating ground signal and is used for measuring a bio-potential signal. For example, the floating ground 108 corresponds to a ground that is not electrically connected to the Earth ground 110, and the floating ground signal is a signal that is referenced to the floating ground 108. For common mode sensing, the sensing circuit can be connected between the floating ground 108 (e.g., point "C") and the Earth ground 110 (e.g., point "D").

Particularly, during the ESU operations, one or more ESU voltage components may be present on each bio-potential input signal (e.g., an electrocardiogram ("ECG") signal), and the ESU voltage components may have some dynamic signal potential with respect to the floating ground 108. Thus, the ESU voltage components that indicate active ESU operations can be detected through differential sensing. Furthermore, during the ESU operations, the floating ground 108 can be floating at a common mode potential of the ESU 102, and may have a high level and a high frequency. The floating ground 108 can then be detected through common mode sensing.

Specifically, when the ESU 102 is activated, it has two output components: (1) a differential voltage 120 (e.g., $V_{diff}$) from a scalpel 122 to a return plate 132, and (2) a common mode voltage 124 ($V_{cm}$) on a patient body 126 with respect to the Earth ground 110. The differential voltage 120 (e.g., \ huff) represents the active "cutting" energy output for the ESU 102. For example, the differential voltage 120 is larger than 100 $V_{p-p}$, and has a frequency value higher than 200 kHz. The common mode voltage 124 is a parasitic output that is generated (e.g., via a parasitic capacitance 128) because the ESU 102 is not perfectly isolated from the Earth.

The patient body 126 presents a differential load to the ESU 102. For example, the differential voltage 120 (e.g., $V_{diff}$) causes a current to flow through the patient body 126 which has internal resistance 134 (e.g., Rb). A right-leg electrode ("RL") brings the body potential to the floating ground 108 through a neutral drive amplifier 106. The patient body 126 also presents a common mode impedance (e.g., 200 pF) to the Earth ground 110, which loads down the ESU common mode excitation. For example, the resulting common mode voltage 124 on the patient is larger than 100 $V_{p-p}$ at high frequencies.

An amplifier 136 for monitoring bio-potential signals is connected to the patient body 126 by placing electrodes at multiple physical locations. A voltage developed on any of the patient electrodes (e.g., left arm ("LA"), right arm ("RA")) with respect to the floating ground 108 can be used to detect ESU operations. As shown in FIG. 1, the LA electrode is used as an example. For example, the voltage 112 on LA can be high-pass filtered and rectified to produce a direct-current ("DC") output to indicate whether the ESU has been activated.

FIG. 2 depicts an example diagram showing an ESU detection circuit. As shown in FIG. 2, the ESU detection circuit 200 includes a high-pass filter for high-pass filtering a voltage signal 212 and a rectifying detector for rectifying the filtered signal to generate a DC output 214 (e.g., a sensing signal for detecting the ESU activities).

Specifically, the voltage signal 212 represents an ESU-related signal, e.g., the voltage 112 on LA, the floating ground 108, etc. The voltage signal 212 has a high level and a high frequency when the ESU 102 is activated. For example, the high-pass filter includes a capacitor 202 and a resistor 204, where a resistor terminal 220 of the resistor 204 is electrically connected to the capacitor 202. The rectifying detector includes a diode 206, a capacitor 208 and a resistor 210. As an example, a capacitor terminal 224 of the capacitor 208 is electrically connected to a resistor terminal 222 of the resistor 204. An anode terminal 226 of the diode 206 is electrically connected to the high-pass filter.

For example, the high-pass filter may pass signals that have a frequency value higher than 200 kHz, and blocks signals that have a frequency value lower than 2 kHz. The frequencies of the ESU signals are usually higher than 200 kHz, and the frequencies of the ECG signals are usually lower than 2 kHz. Thus, the high-pass filter can pass the ESU signals and block the ECG signals. It should be understood that the circuit 200 including the high pass filter and the rectifying detector as shown in FIG. 2 is merely an example, and can be varied in circuit design to meet other system requirements.

The DC output 214 can be monitored by subsequent circuitry (not shown). For example, if the ESU 102 is operating, the DC output 214 increases from 0 V to trigger action to modify bio-potential signal processing to reduce artifacts. Dynamic detection of the ESU operation can allow for implementation of automatic correction algorithms for bio-potential signals. As an example, the bio-potential monitoring system 104 includes a signal processor for processing the bio-potential signals using a signal processing algorithm. The signal processor may modify the signal processing algorithm according to the detection of the activities of the ESU 102 (e.g., an increase in the DC output 214). In one example, the signal processor changes the signal processing of the bio-potential signals linearly or non-linearly.

Other circuit designs may be implemented for the rectifying detector. For example, the rectifying detector can include a half-wave rectifier, a full-wave rectifier, and/or a self-clocked demodulator.

Figure 3:
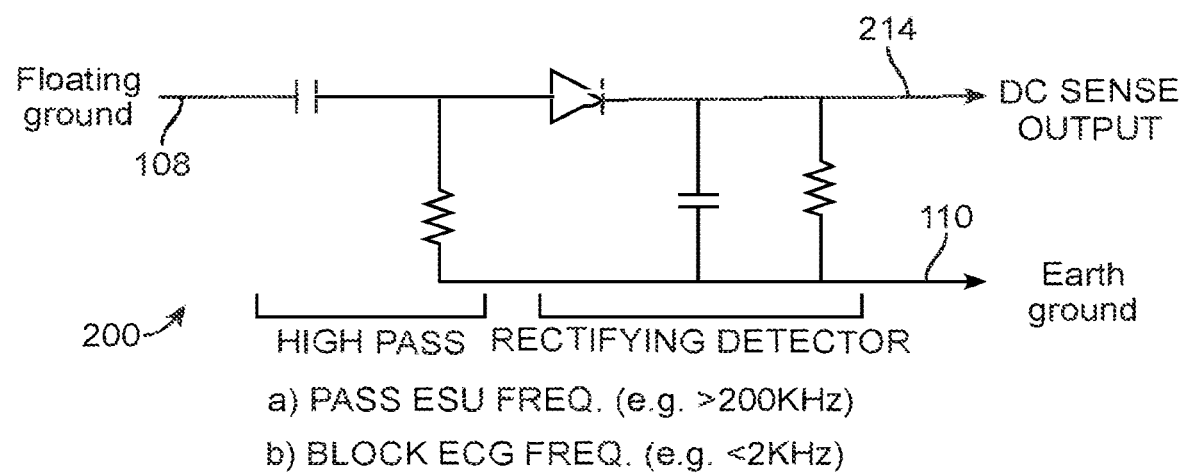
FIG. 3 depicts an example diagram showing the ESU detection circuit for common mode sensing.

FIG. 3 depicts an example diagram showing the ESU detection circuit for common mode sensing. As shown in FIG. 3, the circuit 200 filters the floating ground 108 and rectifies the filtered signal to generate the DC output 214 for ESU detection, where the circuit 200 is biased to the Earth ground 110. During the ESU operations, the floating ground 108 has a high level (e.g., higher than a threshold) and a high frequency with respect to the Earth ground 110, and thus can be detected using the circuit 200.

Figure 4:
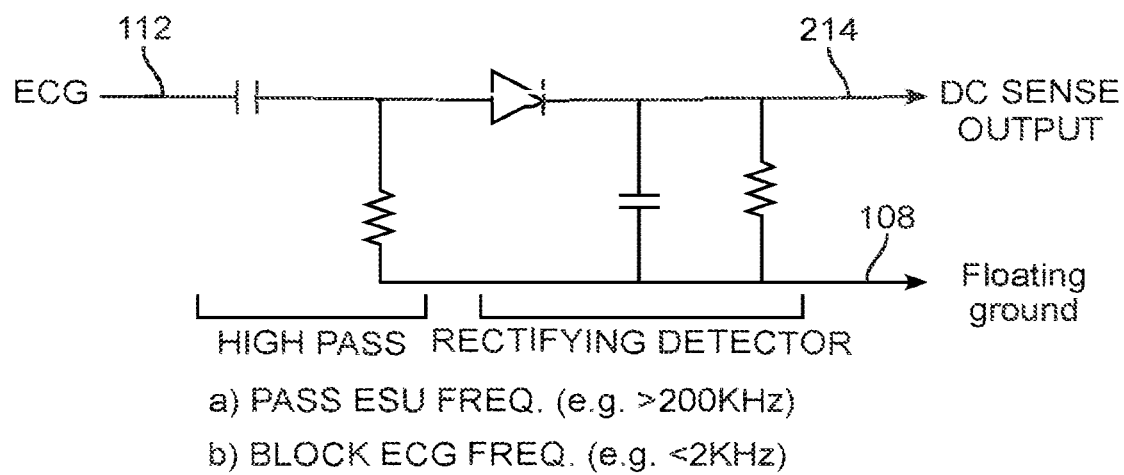
FIG. 4 depicts an example diagram showing the ESU detection circuit for differential sensing.

FIG. 4 depicts an example diagram showing the ESU detection circuit for differential sensing. As shown in FIG. 4, the circuit 200 filters the voltage 112 on LA and rectifies the filtered signal to generate the DC output 214 for ESU detection, where the circuit 200 is biased to the floating ground 108. During the ESU operations, an ESU voltage component can be present on the voltage 112, and the ESU voltage component has a dynamic signal potential with respect to the floating ground 108. Thus, the ESU voltage component that indicates active ESU operations can be detected through differential sensing as shown in FIG. 4.

For example, the voltages described above can be measured relative to the floating ground 108 (not the Earth ground 110). The circuit 200 can be placed within a same electrical isolation region (e.g., a region electrically isolated from the Earth ground 110) as the bio-potential monitoring system 104, so as to greatly simplify circuit design.

One or more aspects or features of the subject matter described herein can be realized in digital electronic circuitry, integrated circuitry, specially designed application specific integrated circuits ("ASICs"), field programmable gate arrays ("FPGAs") computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

We claim:

1. A circuit for detecting an electrosurgical unit signal, the circuit comprising:
 a filter configured to process a bio-potential signal of a patient; and
 a detector configured to output a sensing signal based at least in part on a floating ground signal associated with measuring the bio-potential signal of the patient and an Earth ground for detecting an electrosurgical unit signal,
 wherein the filter and the detector are placed in the same electrical isolation region as circuitry configured to measure and process the bio-potential signal of the patient, the electrical isolation region being electrically isolated from the Earth ground, and
 wherein the detector includes:
  a diode including an anode terminal and a cathode terminal, the anode terminal being electrically connected to the filter,
  a first capacitor including a first capacitor terminal and a second capacitor terminal, the first capacitor terminal being electrically connected to the cathode terminal, the second capacitor terminal being connected to a floating ground corresponding to the floating ground signal, and
  a resistor including a first resistor terminal and a second resistor terminal, the first resistor terminal being electrically connected to the first capacitor terminal, the second resistor terminal being connected to the floating ground.

2. The circuit of claim 1, wherein the filter includes:
 a second capacitor; and
 a second resistor including a third resistor terminal and a fourth resistor terminal, the third resistor terminal being electrically connected to the second capacitor, the fourth resistor terminal being connected to the floating ground.

3. The circuit of claim 2, wherein:
 the second capacitor includes a third capacitor terminal and a fourth capacitor terminal;
 the third capacitor terminal is configured to receive the bio-potential signal of the patient; and
 the fourth capacitor terminal is electrically connected to the third resistor terminal.

4. The circuit of claim 1, wherein:
 the floating ground signal includes a high-frequency component and a low-frequency component.

5. The circuit of claim 4, wherein the filter is configured to pass the high-frequency component and block the low-frequency component.

6. The circuit of claim 4, wherein the low-frequency component is associated with the bio-potential signal of the patient.

7. The circuit of claim 4, wherein:
the high-frequency component corresponds to a frequency value larger than a threshold; and
the low-frequency component corresponds to a low frequency value smaller than the threshold.

8. The circuit of claim 1, wherein the detector is further configured to rectify the filtered floating ground signal to a direct current level.

9. The circuit of claim 8, wherein the electrosurgical unit signal is detected when the direct current level is higher than a threshold.

10. The circuit of claim 1, wherein the detector includes a half-wave rectifier.

11. The circuit of claim 1, wherein the detector includes a full-wave rectifier.

12. The circuit of claim 1, wherein the detector includes a self-clocked demodulator.

13. The circuit of claim 1, further comprising:
a signal processor configured to process the bio-potential signal according to an algorithm.

14. The circuit of claim 13, wherein the signal processor is further configured to change the algorithm based at least in part on the electrosurgical unit signal.

15. The circuit of claim 13, wherein the signal processor is further configured to change the algorithm linearly or non-linearly.

16. The circuit of claim 1, wherein the bio-potential signal corresponds to an electrocardiogram signal.

17. The circuit of claim 1, wherein the bio-potential signal corresponds to an electroencephalograph signal.

* * * * *